United States Patent
Rebentisch

(10) Patent No.: US 9,112,325 B2
(45) Date of Patent: Aug. 18, 2015

(54) CONTACT CONFIGURATION, CONTACT ASSEMBLY, IMPLANTABLE APPARATUS AND ELECTRODE LINE

(75) Inventor: Ronald Rebentisch, Berlin (DE)

(73) Assignee: BIOTRONIK CRM PATENT AG (CH)

( * ) Notice: Subject to any disclaimer, the term of this patent is extended or adjusted under 35 U.S.C. 154(b) by 1827 days.

(21) Appl. No.: 11/927,796

(22) Filed: Oct. 30, 2007

(65) Prior Publication Data

US 2009/0099620 A1    Apr. 16, 2009

(30) Foreign Application Priority Data

Nov. 15, 2006    (DE) .......................... 10 2006 053 729

(51) Int. Cl.
| | |
|---|---|
| *A61N 1/375* | (2006.01) |
| *H01R 24/58* | (2011.01) |
| *H01R 13/33* | (2006.01) |
| *H01R 13/03* | (2006.01) |
| *H01R 107/00* | (2006.01) |

(52) U.S. Cl.
CPC .............. *H01R 24/58* (2013.01); *A61N 1/3752* (2013.01); *H01R 13/33* (2013.01); *H01R 13/03* (2013.01); *H01R 2107/00* (2013.01); *H01R 2201/12* (2013.01)

(58) Field of Classification Search
CPC .............. A61N 1/3752; A61N 1/3754; H01R 2201/12; H01R 24/58; H01R 13/111
USPC ............................ 607/36, 37; 439/7, 290, 909
See application file for complete search history.

(56) References Cited

U.S. PATENT DOCUMENTS

| | | | |
|---|---|---|---|
| 4,156,429 A | 5/1979 | Amundson | |
| 4,199,637 A | 4/1980 | Sado | |
| 4,449,774 A | 5/1984 | Takashi et al. | |
| 4,469,104 A | 9/1984 | Peers-Trevarton | |
| 4,995,389 A | 2/1991 | Harris | |
| 5,070,605 A * | 12/1991 | Daglow et al. ................... | 29/842 |
| 5,074,313 A | 12/1991 | Dahl | |

(Continued)

FOREIGN PATENT DOCUMENTS

| | | |
|---|---|---|
| DE | 2 652 683 A1 | 6/1977 |
| DE | 2 827 595 A1 | 4/1979 |

(Continued)

OTHER PUBLICATIONS

European Patent Office, Search Report for corresponding EP 07020387.2, Mar. 25, 2009.

(Continued)

*Primary Examiner* — Tammie K Heller
(74) *Attorney, Agent, or Firm* — Craig A. Fieschko, Esq.; DeWitt Ross & Stevens S.C.

(57) ABSTRACT

A contact configuration for producing an electrical connection between a plug and a socket, preferably for connecting an electrode to an electronic implantable device (such as a pacemaker), has a contact section on the plug and/or the socket. The contact section includes metallic conductive fibers which project between the plug and socket when the socket receives the plug. The contact configuration has a high degree of redundancy in providing electrical communication between the socket and plug, and high contact stability under mechanical load. In addition, friction corrosion is avoided.

26 Claims, 6 Drawing Sheets

(56) References Cited

U.S. PATENT DOCUMENTS

| | | | |
|---|---|---|---|
| 5,730,628 A * | 3/1998 | Hawkins | 439/843 |
| 5,795,165 A | 8/1998 | Jarl | |
| 6,312,297 B1 | 11/2001 | Lorkowski | |
| 6,498,952 B2 | 12/2002 | Imani et al. | |
| 7,195,523 B2 | 3/2007 | Naviaux | |
| 2002/0022389 A1 | 2/2002 | Hikata et al. | |
| 2002/0128692 A1 | 9/2002 | Imani et al. | |
| 2003/0050549 A1 | 3/2003 | Sochor | |
| 2005/0261745 A1 | 11/2005 | Tvasuka et al. | |
| 2006/0004419 A1 | 1/2006 | Olbertz | |
| 2006/0047322 A1 | 3/2006 | Naviaux | |

FOREIGN PATENT DOCUMENTS

| | | |
|---|---|---|
| DE | 10 2004 017 659 A1 | 10/2005 |
| EP | 0 453 117 A1 | 10/1991 |
| EP | 0747999 A | 12/1996 |
| EP | 1 062 986 A2 | 12/2000 |
| WO | WO 0064535 A | 11/2000 |
| WO | WO 2005/014104 A1 | 2/2005 |
| WO | WO 2005/014107 A1 | 2/2005 |
| WO | WO 2005/014108 A1 | 2/2005 |
| WO | WO 2005/105207 A2 | 11/2005 |

OTHER PUBLICATIONS

Van Dijk, P., "Critical aspects of electrical connector contacts," Proceedings of the 21$^{st}$ International Conference on Electrical Contacts, Sep. 9-12, 2002, Zurich, Switzerland, Swiss Electronic Engineering Association, Edited by Werner Johler, Fehraltorf: SEV, 2002—VIII, pp. 19-555, ISBN: 3-9522504-0-6.

McBride, J., et al., "Intermittency events in bio-compatible electrical contacts," published in Electrical Contacts, 2005, Proceedings on the 51$^{st}$ Holm Conference, pp. 75-81, ISBN: 0-7803-9113-6.

\* cited by examiner

CONTACT CONFIGURATION, CONTACT ASSEMBLY, IMPLANTABLE APPARATUS AND ELECTRODE LINE

FIELD OF THE INVENTION

The present invention relates to a contact configuration for producing an electrical connection between a plug (e.g., an essentially cylindrical plug) and a socket (e.g., an essentially hollow-cylindrical socket), preferably for connecting an electrode to an electronic implantable apparatus. Preferably, the contact configuration forms either the contact section of the plug or the contact section of the socket, the socket contact section having an opening into which the plug is insertable, the contact configuration having at least one contact element, the contact element comprising a braid (e.g., a woven mat) having fibers which have metallic conductivity. Furthermore, the present invention relates to a contact assembly, an implantable apparatus and an electrode line.

BACKGROUND OF THE INVENTION

Implantable apparatuses which are provided with electronic devices, such as circuit boards or the like, are frequently used in the field of medicine. Electronic devices such as cardiac pacemakers and defibrillators, or neurological devices, such as cerebral pacemakers for deep brain stimulation, spinal cord stimulation devices, TENS (transcutaneous electrical nerve stimulators), or devices for muscular stimulation therapy, as well as diagnostic apparatuses, which assay the chemical properties of the blood of the patient or other body parts or other body characteristics, use electrodes which are guided through the body of the patient and are electrically connected to the implantable apparatus. The implantable electronic apparatus often has an essentially socket-shaped or hollow-cylindrical connection apparatus (socket, contact pin) for this purpose, in the form of a contact assembly, into which the plug of the electrode line is inserted to produce an electrical connection between the electrode and the electronic apparatus situated in the implantable apparatus. The connection apparatus is often referred to as a header. An essentially cylindrical plug having a contact assembly, which is inserted into the socket to produce the electrical connection, is also provided on the electrode line which has the electrode.

In the future, multi-pole plugs having more than two poles will be increasingly used. For example, the plug according to the standard IS-4 is a 4-pole plug which has an essentially cylindrical shape and has four electrically conductive contact sections which are situated neighboring one another in the axial direction.

An essentially cylindrical plug, which may be inserted into a socket, is specified in U.S. Pat. No. 4,469,104. For this purpose, the socket has an essentially cylindrical opening. Three contact configurations situated one behind another in the direction of the longitudinal axis are provided on the multi-pole plug, which are each separated from one another by insulating areas. A conductive ring in the form of a woven metal toroid is situated in a retention element provided with a groove. The toroid is produced from a leaf-shaped woven metal. After the toroid has been shaped by rolling up the leaf-shaped material, the material is welded together on its ends to form a closed elastic ring. The conductive ring is situated in the retention element in such a way that it projects slightly beyond the lateral surface of the adjoining areas of the plug. After the plug is inserted into the opening of the contact assembly, the conductive ring contacts the contact sections situated on the socket, each of which has the form of a metal ring. An electrical connection is thus produced between the particular contact configuration on the plug and the contact section of the socket to electrically connect the electrode to the electronic apparatus in the implantable device.

In the publication WO 2005/014108, a contact configuration for connecting an electrode and an implantable medical device is described. The contact configuration has a connection clip which comprises a single wire and is shaped in such a way that it has a first spring arm and a second spring arm. Both spring arms adjoin an upper curved section which forms the upper section of the connection clip. The spring arms have essentially linear lateral sections, which extend from the upper curved section to a lower curved section. The connection clip is situated in a partially bent-up position in the housing of the contact configuration having a through opening. The connection clip is situated in the housing of the contact configuration in such a way that it projects slightly inward in the radial direction from the housing. The housing is shaped for this purpose in such a way that after the plug is inserted into the opening of the contact configuration, the connection clip is pressed further outward in the radial direction, so that a connection between plug and electronic device is produced.

An implantable electronic device having a regulating device for the plug and an electrode line connectable to the device is known from the document EP 1 062 986 B1. The electronic device has an essentially socket-shaped connection apparatus for the plug of the electrode line to the regulating device, which is formed by a manually operable, eccentrically mounted clamping cam and a contact element provided in the connection apparatus for the different pole of the plug of a coaxial electrode line to be connected to the cardiac pacemaker. The eccentrically mounted clamping cam is operationally linked at its edge to the contact element, so that a rotational movement of the clamping cam is transmitted to the contact element. The contact element, which encloses the different pole of the plug in a formfitting way, is thus reversibly deformed in such a way that a friction-locked connection results between the different pole and the contact element, which fixes the plug inside the connection apparatus and simultaneously ensures a good electrical contact between the contact element and the different pole of the plug.

An electrical connector, in particular a medically implantable electrical connector having a housing and a through hole is known from the publication WO 2005/105207 A2. A spring is situated in a groove of the housing, which is used for the purpose of scraping off a coating (typically an oxide layer) from the surface of the groove and the plug surface, so that a reduced resistance and a reduced resistance variability are achieved. In particular, the spring is implemented as a diagonally lying coiled spring.

An electrical contact having a spring ring is also known from the publication US 2006/0047322 A1. This publication discloses a contact assembly having multiple contact configurations having electrically conductive spring rings, which are provided in corresponding depressions of the contact configurations.

A contact assembly which has multiple contact configurations having annular spring contacts is described in U.S. Pat. No. 4,995,389.

A contact configuration for connecting an electrode line to an implantable device is known from the publication DE 10 2004 017 659 A1. The contact configuration has an electrical terminal socket having a socket longitudinal axis and at least one opening for inserting a plug along the socket longitudinal axis. A one-piece metallic spring contact tongue having spring contact tongue sections running transversely to the spring deflection direction, which are connected to one another by coil sections, is provided as the contact element. The spring contact tongue is particularly used in such a way that it has a wavy shape, such as an S-shaped wavy shape.

A contact element made of a one-piece metallic spring contact tongue is also specified in the publication US 2005/0261745 A1. Multiple contact elements are bent here in such a way that their end section extends into the opening and forms a tangent on an imaginary circle, which has a smaller diameter than the opening of the electrode configuration for the plug. In this publication, a second variation of a contact configuration is also described, in which the contact elements comprise rod-shaped elements, whose end sections are directed away from the opening for the plug. Analogously to the leaf-shaped elements, the rod-shaped elements are bent in such a way that they form a tangent on an imaginary circle which has a smaller diameter than the cross-section of the plug opening.

A further possibility for a contact configuration is disclosed in the publication US 2002/0128692 A1. The contact configuration contains annular spring elements in which circular openings are provided. Spherical contact elements are situated in the circular openings, which are pressed by the spring action of the spring in the direction away from the opening, but project somewhat therein, so that a contact is produced between the inserted plug and the metal balls.

High-precision and therefore costly manufacturing devices are necessary for producing the above-mentioned contact configurations having metallic spring elements or tongues. These contact elements are typically from a strip material produced via a punching-bending process in a progressive composite die. For example, a rectangular sheet metal strip is generated, which is reshaped over the longer side in such a way that it becomes the lateral surface of a tube which is not entirely closed. By punching out segments in the direction of the shorter side from this lateral surface, a specific number of webs arise. These webs are reshaped to half the height of the lateral surface in such a way that they project radially inward uniformly and thus form a constriction in the lateral surface, via which the electrical contact may occur later. A contact element of this type does not have a defined radius, however, via which a contact force on a cylindrical plug may be adjusted. A functional contact assembly first arises when a contact element is inserted into the hole of a dimensionally stable sleeve with radial pretension.

The contact materials which are common in everyday electronic apparatuses and are therefore also cost-effective may not be used in long-term implants, because in addition to the rather general criterion of corrosion stability, the criterion of biocompatibility must also be fulfilled. For materials which are not frequently used, however, the continuous availability of the materials needed for running production may be problematic.

For a stable electrical contact of a plug-in connection, a macroscopic minimum contact pressure between the contact partners of plug and socket is primarily needed. This minimum contact pressure for a single contact is a function of the materials used, in a first approximation, a normal force of greater than 1 N may be used. If a minimum contact pressure of this type is not achieved, electrically insulating cover layers of the material surfaces may not be removed in the contact area and, in addition, the long-term stability of the electrical contact is not ensured.

In the constructive mechanical design of a plug contact system, however, the plugability must also be ensured. A parameter for this purpose is the maximum permissible insertion force. The spring rigidity of the contact elements may not be increased arbitrarily to thus achieve better electrical contact security, because otherwise problems may occur in the plugging procedure.

Therefore, for a stable electrical contact it is necessary for the mechanical tension built up upon insertion of the cylindrical plug (contact end) to be so great that electrically insulating cover layers which interfere in the contact area are removed, so that the contact partners may come into direct metallic contact. For chronological consistency of the electrical contact resistance, the contact area thus produced must remain metallically conductive over the entire duration of the contact. It is accordingly to be ensured by the construction that such a contact may not lift off (breathe) in the event of weak mechanical tension and under radial mechanical load. However, it is also to be ensured that a contact of this type does not begin to rub in the event of strong mechanical pretension and axial mechanical load, because friction corrosion (fretting) may thus occur.

SUMMARY OF THE INVENTION

An object of the present invention is therefore to provide a contact configuration which has a high degree of redundancy in the contacting and high contact stability under mechanical load. In addition, friction corrosion is to be avoided. An analogous object also exists in regard to the contact assembly, the implantable apparatus, and the electrode line.

This object can be achieved according to the present invention by a contact configuration in which at least one end of multiple fibers of the fiber braid of the contact element project into the opening and/or project outward away from the lateral surface.

The present invention is based on the finding that only a fraction of the contact area mechanically produced by the contact pressure is active for the electrical contact at all. The electrically active areas standing in indirect metallic contact are referred to as "a-spots" or "contact spots" (P. van Dijk, 'Critical aspects of electrical connecter contacts'; published in: International Conference on Electrical Contacts <21, 2002, Zurich> Proceedings/21st International Conference on Electrical Contacts: 9-12 Sep. 2002, Zurich, Switzerland/ [Schweizerischer Elektrotechnischer Verein. [Swiss Electronic Engineering Association] Ed. by Werner Johler].—Fehraltorf: SEV, 2002.-VIII, pages 19-555, ISBN: 3-9522504-0-6 Text may be found under http://www.pvdijk-.com/pdf/21thiceccriticalaspects.pdf, viewed on 27.10.2006; and J. W. McBright and C. Maul, 'Intermittency events in bio-compatible electrical contacts', in: "Electrical Contacts, 2005, Proceedings on the 51st Holm Conference, pages 75-81, ISBN 0-7803-9113-6). It is described in the cited literature that at a normal force of 1 N, an a-spot diameter of at most 75 µm is to be expected. The electrical contacting therefore occurs via metallic contact points having a dimension of approximately 10 to 20 µm diameter. To remove the cover layers situated on the contact areas, normal forces of approximately 1 N are needed. At least three contact points—distributed as uniformly as possible around the circumference—are necessary for the axial guiding of the cylindrical plug. It may be assumed in this case that the three contact forces are of equal absolute value. If more than three contact points are constructively provided, uneven distribution of the normal forces in the contact points may occur because of production and manufacturing tolerances, so that it may not be assumed that the cover layers may be effectively penetrated in all contact points. These disadvantages are corrected by the use of multiple flexible contact fibers according to the present invention, in that due to the multiple flexible fibers, a normal force which is constant in broad ranges may be set in the contact points.

The contact configuration according to the present invention has the advantage that the contact areas are reduced to the "real" contact areas (a-spots) and in this way a higher degree of redundancy in contacting and higher contact stability under mechanical load are achieved. The contact configuration according to the present invention, which is thus reduced to the active contact areas, is additionally therefore advantageous because due to its design, the influence of the constructively influencable characteristics, the influence of material parameters, and the influence of process parameters during the production are minimized and the required materials have good availability on the market. In addition, gap corrosion is prevented by the contact configuration according to the present invention The contact configuration especially preferably comprises a flexible fiber mat (fiber web) having a predefined thickness. The thickness of the fiber mat is preferably between 0.5 and 1.5 mm (inclusive), especially preferably between 0.7 and 1.2 mm (inclusive). Flexible mats of this type can be produced using typical, classical processing methods of the textile industry as woven fabric, knitted fabric, or scrim and, for example, have an ordered woven fabric. The fibers having metallic conductivity may also be formed into a nonwoven material having so-called tangled fibers, i.e., disorderly fibers, preferably having uniform area density.

The contact configuration for the socket contact section is preferably provided with a through opening running in the longitudinal direction of the socket, which has an essentially round cross-section. An opening of this type is producible especially simply. The opening preferably has a mean diameter DO, which is smaller than the diameter of the plug contact section intended to be situated in the opening in the area of the contact configuration. In this way, the required normal forces between contact element and counter contact on the plug are produced. The mean diameter DO of the continuous opening is especially preferably smaller than the diameter of the plug contact section by at least 0.3% and at most 3.5% of the diameter of the plug contact section.

In an especially preferred exemplary embodiment, the opening has one or more slots around its circumference, preferably three slots, which are situated at an interval of approximately 120°. The contact stability on one hand and the plugability of the contact configuration on the other hand are ensured. The slot width and configuration and thus the normal forces may be set individually. The slot width is especially preferably between 10% and 40% of the circumference of the through opening.

In further exemplary embodiments, the through opening may also have other cross-sectional shapes, for example, a pentagonal or hexagonal shape. Analogously to the embodiment having the round cross-section, slots may be incorporated in contact element of this type or the width of the opening may be designed as correspondingly smaller than the diameter of the corresponding plug section.

In a further preferred exemplary embodiment, the contact element for the plug contact section comprises the same material as the contact element for the socket contact section, preferably a matted fiber braid, which has an essentially circular cross-section. To implement the required minimum contact pressure, the fiber braid has a mean diameter DK of its cross-section which is greater than the diameter of the opening of the socket contact section which is intended for positioning the plug contact section in the area of the contact configuration. The mean diameter DK of the fiber braid is especially preferably larger than the diameter of the opening by at least 0.3% and at most 3.5% of the diameter of the opening.

The contact configurations according to the present invention may be produced especially simply by producing the through opening of the contact element of the socket contact section and/or the outer edge or the outer edges of the contact element of the plug contact section using laser cutting or mechanical punching. In laser cutting, the energy of the laser may be set for this purpose in such a way that, in an especially pre-ferred exemplary embodiment, at least a part of the multiple fibers of the fiber braid project into the opening and/or project outward away from the lateral surfaces with a rounded end. The surface roughness is thus advantageously minimized.

Especially in the case of the contact configuration for a socket contact section, the contact configuration may have a retention element in the form of a frame made of a metallic material in which the fiber braid is set. A contact configuration of this type has the advantage that it is easily producible.

On its outer edges, especially in the case of the contact element for a socket contact section, the fibers of the fiber braid may be fixed using a thermal method, for example, using a laser.

The mean diameter d of the fibers is at most 75 μm, preferably $2 \leq d \leq 50$ μm, more preferably $10 \leq d \leq 50$ μm, particularly preferably $10 \leq d \leq 35$ μm. Using these fiber diameters, the fiber diameter is advantageously reduced to the dimension of the particular a-spots, over which the electrical contact is active.

Especially suitable materials in regard to the conductivity, corrosion resistance, and biocompatibility are used if the fibers of the fiber braid at least partially comprise a material of the group platinum, iridium, and stainless steel according to relevant standards about implant materials (ISO; ASTM), preferably stainless steel 316L or stainless steel 316L-VM, titanium alloy, conductive plastic, carbon fibers, conductive ceramics, or a mixture of at least two materials of this group. The degree of filling of the fiber braid is advantageously between 50% and 80% (inclusive), preferably between 50% and 70% (inclusive).

At least 60 contact points with the plug contact section and/or the socket contact section are especially preferably producible using the fibers of the fiber braid projecting into the through opening or projecting away from the lateral surfaces.

The fiber braid may be handled well in the production of the contact configuration if it is filled with silicone or a flexible electrically insulating plastic. In addition, the propagation of bodily fluids along the plug and socket longitudinal axis is effectively prevented.

The above object is also achieved according to the present invention by a contact assembly for a plug or a socket having one or more contact configurations according to the present invention. The contact assembly according to the present invention provides a high degree of redundancy in the contacting and increases the contact stability under mechanical load. In an especially preferred exemplary embodiment, a contact assembly having multiple contact configurations has an electrically insulating configuration between them, to avoid errors in current conduction and to insulate the individual contact configurations from one another.

In a further preferred exemplary embodiment, the contact assembly also has a seal configuration, which is used for sealing the implantable apparatus to bodily fluids.

A contact assembly having multiple contact configurations has a distance 1 between the centers of the contact elements of two neighboring contact configurations in the axial direction of the contact assembly between 2 and 6 mm (inclusive), preferably between 3 and 5 mm (inclusive), especially preferably between 4 and 5 mm (inclusive). The standard for multiple plugs and plug sockets, such as the IS-4 standard, is fulfilled by this design of the contact assembly.

The above object is additionally achieved according to the present invention by an implantable apparatus having a socket contact assembly according to the present invention and an electronic apparatus having at least one terminal, the at least one terminal of the electrical apparatus being electrically connected to a contact configuration. The above object is also correspondingly achieved according to the present invention by an electrode line having a plug situated on one end having a plug contact assembly according to the present invention, the electrode being electrically connected to at least one of the contact configurations. The implantable apparatus according to the present invention, such as a cardiac pacemaker, a defibrillator, a neurological apparatus, or a muscle stimulation apparatus, and the electrode line according to the present invention allow the production of reliable electrical contacts which are especially stable under mechanical load.

Further goals, features, advantages, and possible applications of the present invention result from the following description of exemplary embodiments and the drawings. All features described and/or shown in the figures form the subject matter by themselves or in any arbitrary combination, independently of their summary in the claims or what they refer back to.

BRIEF DESCRIPTION OF THE DRAWINGS

FIG. 1 shows a cardiac pacemaker 1 having a terminal housing (header) 3 and an electrode conductor 4. The electrode conductor 4 is plugged into the socket 5, which is implemented as a plug socket, using its plug situated on one end of the electrode conductor 4. In this way, the electrode situated on the end of the electrode conductor 4 diametrically opposite the plug (not shown) is electrically connected to the electronic apparatus situated in the housing 6. In addition, the battery of the cardiac pacemaker, which supplies the electronic apparatus, such as the electronic circuit board, with voltage, is located in the housing 6.

Figure 1:
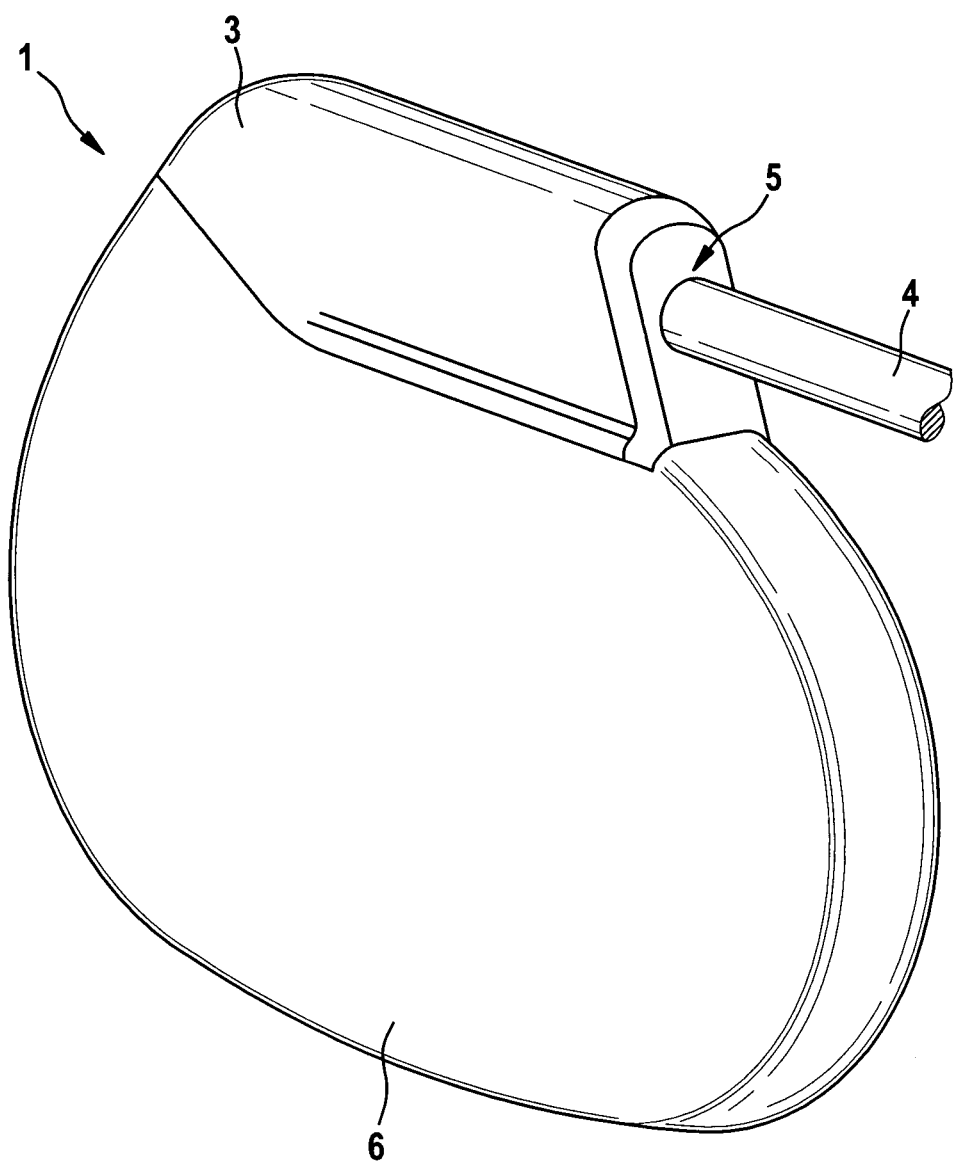
FIG. 1 schematically shows an implantable apparatus according to the present invention in a section of an electrode line according to the present invention in a perspective view from the side, FIG. 2 schematically shows a longitudinal section through a contact assembly of a socket according to the present invention, FIG. 3 schematically shows a detail from the cross-section from FIG. 2, FIG. 4 schematically shows a contact element for a contact configuration according to the present invention for a socket contact section in a view from above, FIG. 5 schematically shows a detail from a section through the contact element from FIG. 4, FIGS. 6 and 7 schematically show further exemplary embodiments of contact elements for a contact configuration of a socket contact section according to the present invention, FIG. 8 schematically shows an exemplary embodiment of a contact assembly for a plug according to the present invention in a view from the side, and FIG. 9 schematically shows a contact element of a contact configuration of the contact assembly according to the present invention from FIG. 8.
Figure 2:
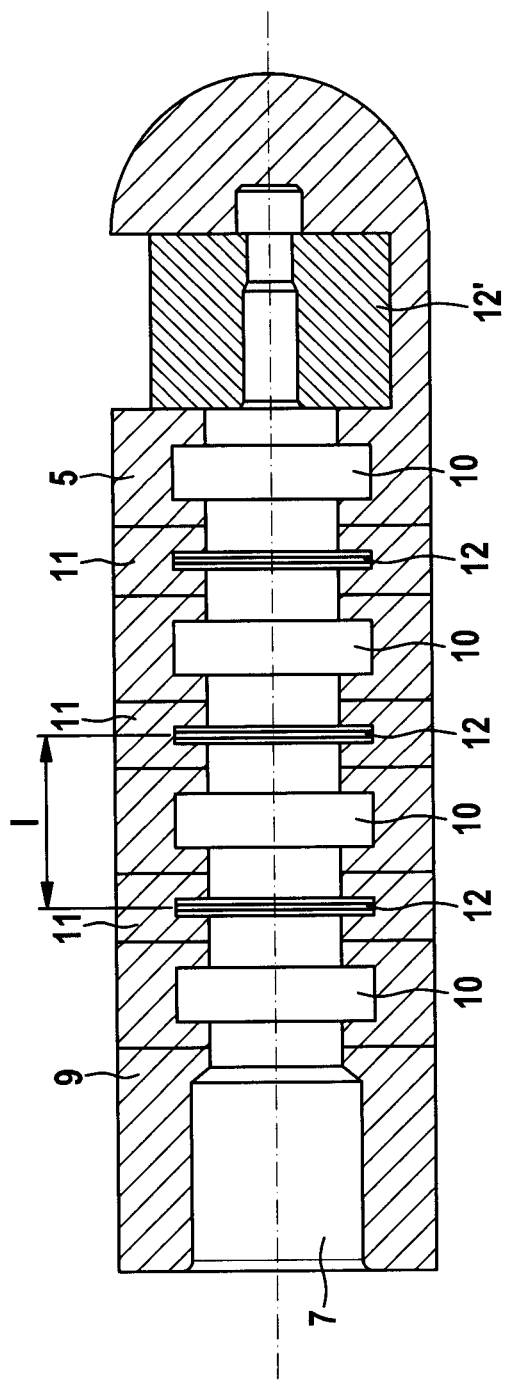

A longitudinal section through a contact assembly implemented as a socket 5 is illustrated in FIG. 2. The socket 5 has a through opening 7 which has multiple sections having different, essentially circular cross-sections (different diameters). The opening 7 ends in the forward end area of the socket 5. The socket essentially comprises insulating material 9 in its areas surrounding the opening 7, in which seal configurations 10 and contact configurations 11 are situated alternately one behind the other in the direction of the longitudinal axis. In the exemplary embodiment of a socket 5 illustrated in FIG. 2, three contact elements 12 having a low thickness (situated in the longitudinal direction of the socket 5) and a further, wider contact element 12' situated on the front end of the socket are situated one behind the other. Each contact element is situated in a contact configuration 11 and is fixed therein in using a retention element. The socket shown is intended for a 4-pole plug. The interval of two centers of the contact elements 12 in the direction of the longitudinal axis of the socket 5 is identified by the letter l in FIG. 2.

Figure 3:
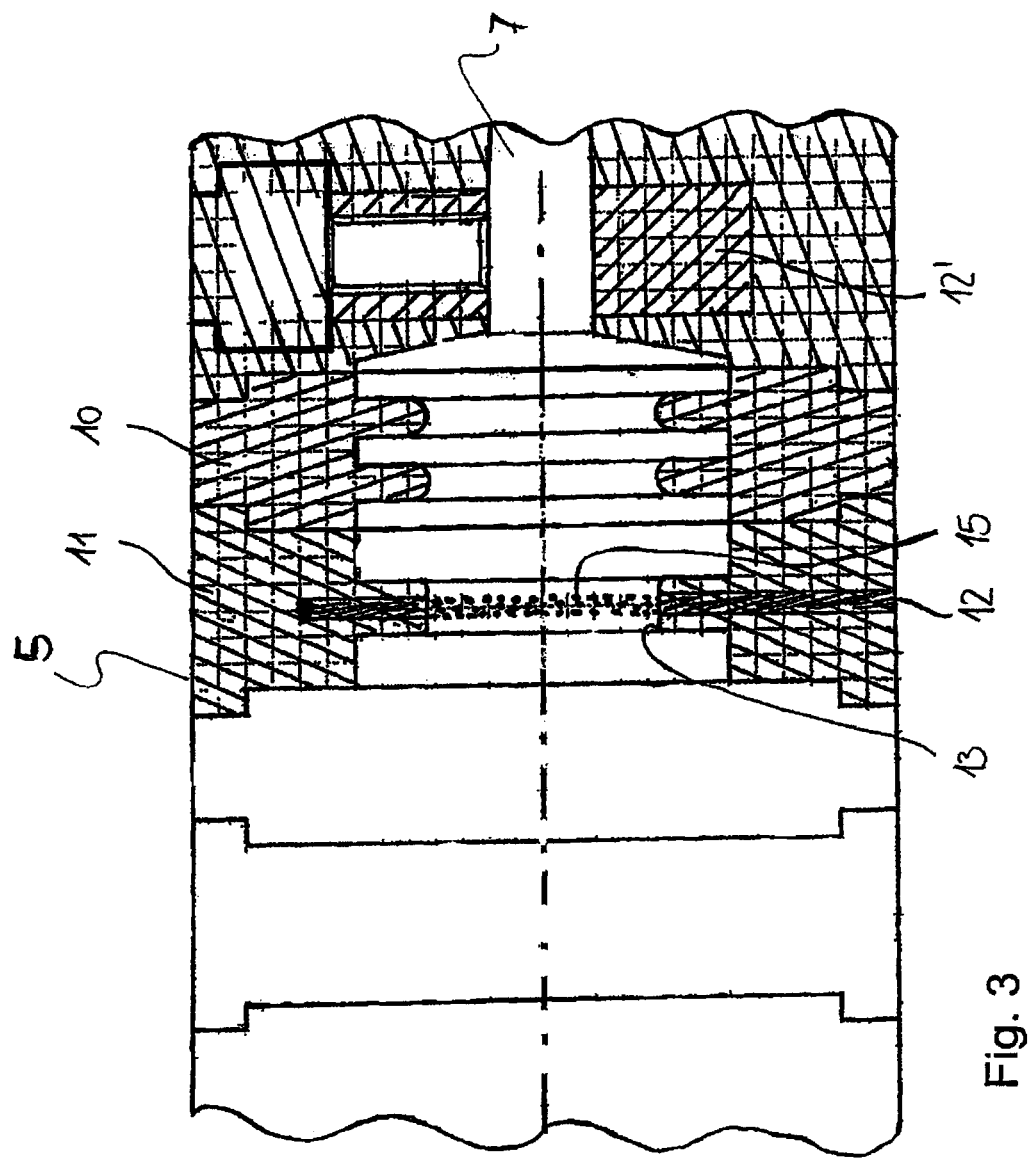

A detail of the socket 5 illustrated in FIG. 2 is shown in FIG. 3. Before the opening 7 tapers in the direction of the forward end, a seal configuration 10 is provided as a segment of the socket. In front of this, in the direction of the insertion opening of the socket 5, a contact assembly 11 having a centrally situated contact element 12 in the form of a flexible fiber braid (mat) is provided, which has a circular opening 13. The ends of the fibers 15 of the fiber braid projecting into the opening come into contact therewith when the plug is plugged in. The contact element made of the fiber braid, which comprises metallic fibers, is held in the contact configuration 11 using the retention element (not shown), for example, in the form of a metallic frame, in such a way that its largest dimension runs approximately perpendicularly to the longitudinal axis of the socket 5.

Figure 4:
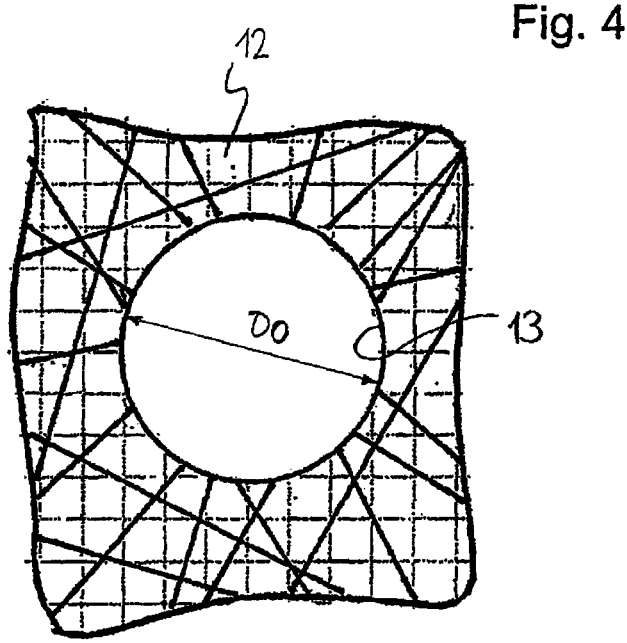

A detail of the contact element 11 comprising the flexible fiber braid of irregularly situated fibers 15 having the circular opening 13 is shown once again separately in FIG. 4. The mean diameter DO of the circular opening is shown in the drawing. It extends from one edge of the circular opening 13 to the diametrically opposite edge and runs through the center point of the opening 13.

Figure 5:
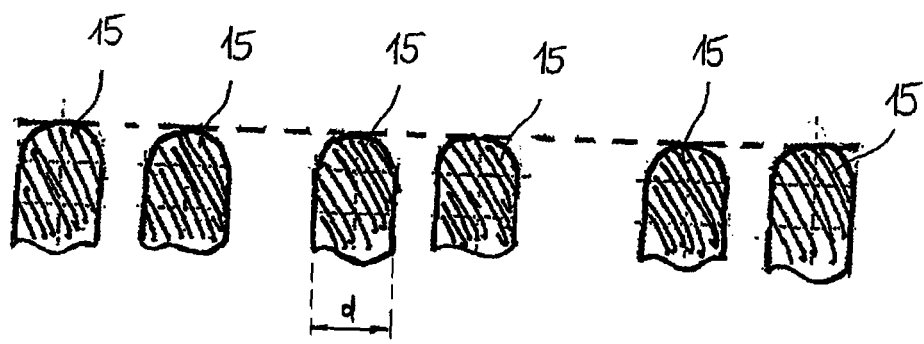

FIG. 5 shows individual fibers 15 having a mean diameter d, which project into the opening 13 and implement the boundary shown by a dashed line. It may be seen that the fibers which project into the opening have a rounded end. This may be achieved by setting the energy of the laser, using which the opening is cut out of the fiber mat, appropriately, so that the material of the fibers melts or softens.

Figure 6:
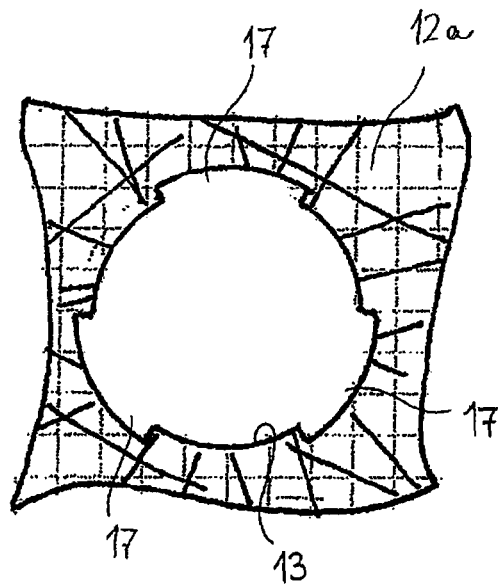
Figure 7:
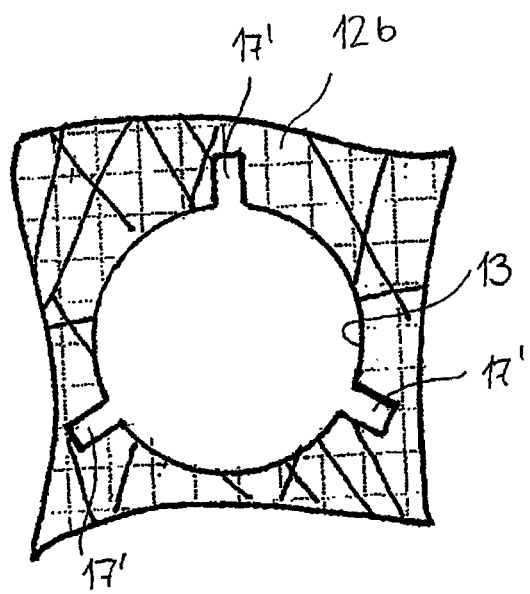

Further exemplary embodiments of contact elements 12a and 12b are illustrated on the basis of FIGS. 6 and 7. The contact elements 12a and 12b have slots 17 which have differing lengths around the circumference. The length of the three slots of the contact elements 12a in FIG. 6 is a total, compared to the total circumference of the opening 13, of approximately half of the total circumference. The slots are situated at an interval of approximately 120° in relation to their particular center of the longitudinal extension on the circumference of the opening. The slots 17' of the contact element 12b are also provided at an interval of 120° in FIG. 7. These slots have a significantly smaller extension in the direction of the circumference of the opening 13 compared to the exemplary embodiment in FIG. 6. However, the depth of the slots 17' in the radial direction is greater than the slots 17 of the exemplary embodiment in FIG. 6. The slots 17 may extend up to the border of the contact element 12a, 12b. The slots 17, 17' run essentially in the radial direction. The flexibility of the contacting in relation to mechanical interfering influences may be adjusted by the design of the slots; "breathing", i.e., the brief separation of the contact points, and the friction of the contact points, so-called fretting, may thus be suppressed.

Figure 8:
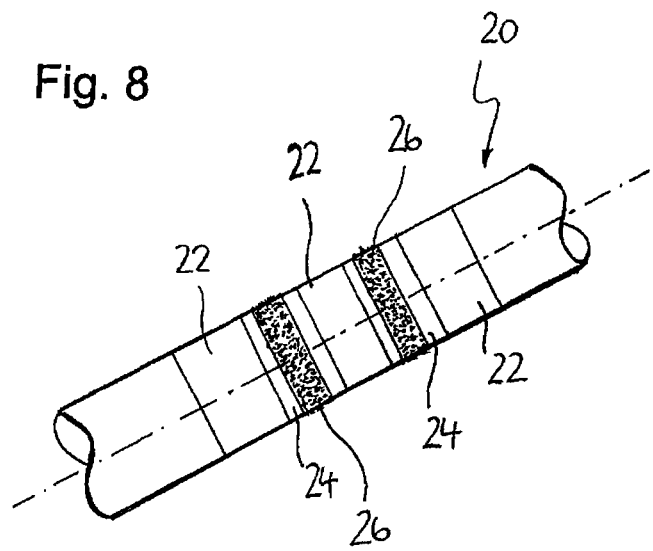
Figure 9:
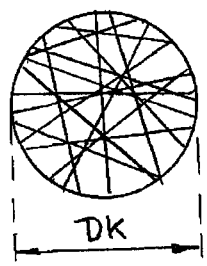

A section of a plug 20 which may be plugged into a socket 5 is shown in FIG. 8. The plug 20 is shaped essentially cylindrically and has insulating areas 22 and contact configurations 24 alternately along its longitudinal axis. Each contact configuration has a contact element 26 in the form of a fiber braid mat having an essentially circular cross-section, which is attached in a retention element (not shown). The fibers on the outer edges of the contact element 26 forming the external circumference project away from the lateral surface of the plug 20 and allow the contact with corresponding counter contact surfaces in a socket. The contact element 26 is shown once again separately in a view from above in FIG. 9. Furthermore, the mean diameter DK is shown, which extends from one outer edge of the contact element 26 up to the other outer edge and passes through the center point of the contact element 26.

In a special exemplary embodiment, the fibers of the mat are filled with a flexible, electrically insulating plastic or silicone. This increases the insertion forces and the rigidity of the fiber disk. An area is thus generated which builds up the electrical contact in the area and, in addition, prevents the propagation of liquid in the direction of the plug longitudinal axis. To fill up the fiber braid with silicone, it is placed in a mold. The desired mold is subsequently filled up with silicone or elastomers, e.g., polyurethane, using injection molding. To keep the opening free, a core may be situated in the opening. The entire plug may especially preferably be produced using injection molding.

Surprisingly, when the plug is plugged in, the projecting fiber ends claw into the particular counter contacts thereof, so that a pretension is generated.

The fiber mat may be fixed using laser soldering on the outer edges. The required cross-sectional shapes of the fiber mat may also be produced using photoetching.

Good electrical contacts may also be produced using the contact configuration according to the present invention for defibrillators, which sometimes operate at voltages of approximately 750 V.

Preferred versions of the invention have been described above in order to illustrate how to make and use the invention. The invention is not intended to be limited to these versions, but rather is intended to be limited only by the claims set out below. Thus, the invention encompasses all different versions that fall literally or equivalently within the scope of these claims.

What is claimed is:

1. A contact configuration for producing an electrical connection between a plug and a socket for an implantable medical device, the contact configuration including:
   a. a plug having an outer plug diameter,
   b. a socket having an inner socket diameter, the socket being configured to receive the plug, with the plug traveling along an insertion axis when received within the socket,
   c. an electrically conductive contact section provided on at least one of:
      (1) the outer plug diameter, wherein the contact section includes fibers protruding outwardly therefrom, or
      (2) the inner socket diameter, wherein the contact section includes fibers protruding inwardly therefrom,
      the fibers defining a mat extending along planes oriented substantially perpendicular to the insertion axis, wherein substantially all of the fibers have lengths extending in directions oriented more perpendicularly to the insertion axis than parallel to the insertion axis.

2. The contact configuration of claim 1 wherein the fiber mat has a thickness between approximately 0.5 and approximately 1.5 mm.

3. The contact configuration of claim 1 wherein the fibers of the contact section each have a substantially circular cross-section.

4. The contact configuration of claim 1 wherein the contact section is formed of a layer of conductive fibers set within a conductive frame.

5. The contact configuration of claim 1 wherein the mean diameter of the fibers is less than approximately 75 µm.

6. The contact configuration of claim 1 wherein the contact section generates at least 60 contact points between the plug and the socket when the plug is fully inserted within the socket.

7. The contact configuration of claim 1 wherein at least some of the interstices between adjacent fibers are filled with a flexible, electrically insulating material.

8. The contact configuration of claim 1 wherein the plug and the socket each include at least one electrically conductive contact section.

9. The contact configuration of claim 8 wherein one of the electrically conductive contact sections of the plug align and electrically communicate with one of the electrically conductive contact sections of the socket when the plug is fully inserted within the socket.

10. The contact configuration of claim 1 wherein the socket is defined within an electronic apparatus configured to be implanted within a living body.

11. The contact configuration of claim 1 wherein the plug is defined upon an electrode line configured to be at least partially implanted within a living body.

12. The contact configuration according to claim 1 wherein the contact section is provided on the outer plug diameter, and wherein the contact section on the outer plug diameter is:
   a. formed of radially outwardly protruding fiber free ends, and
   b. in contact with the fibers of the mat when the plug is fully received within the socket.

13. A contact configuration for producing an electrical connection between a plug and a socket for an implantable medical device, the contact configuration including:
   a. a plug having an outer plug diameter,
   b. a socket having an inner socket diameter, the socket being configured to receive the plug,
   c. an electrically conductive contact section provided on the inner socket diameter, wherein the contact section includes fibers protruding inwardly from the inner socket diameter, the fibers having:
      (1) lengths oriented to define a planar fiber mat:
         i. with the plane of the mat being oriented substantially perpendicular to an insertion axis along which the plug travels when received within the socket, and
         ii. having an opening formed therein, the opening having a mean opening diameter smaller than a portion of the outer plug diameter which is situated in the opening when the plug is fully inserted within the socket; and
      (2) free ends with lengths protruding radially inwardly from the circumference of the opening.

14. The contact configuration of claim 13 wherein the opening has one or more radially outwardly extending slots defined therein around its circumference.

15. The contact configuration of claim 13 wherein at least some of the interstices between adjacent fibers are filled with a flexible, electrically insulating material.

16. The contact configuration of claim 13 wherein the socket is defined within an electronic apparatus configured to be implantable within a living body.

17. The contact configuration of claim 13 wherein the plug is defined upon an electrode line configured to be at least partially implantable within a living body.

18. A contact configuration for producing an electrical connection between a plug and a socket for an implantable medical device, the contact configuration including:
   a. a plug having an outer plug diameter,
   b. a socket having an inner socket diameter, the socket being configured to receive the plug,
   c. an electrically conductive contact section provided on the inner socket diameter, wherein the contact section includes fibers protruding inwardly from the inner socket diameter, the fibers having:
      (1) lengths oriented to define a planar fiber mat having an opening formed therein, with the plane of the mat being oriented substantially perpendicular to an insertion axis along which the plug travels when received within the socket, and
      (2) free ends with lengths protruding radially inwardly from the circumference of the opening,
      wherein the opening has one or more radially outwardly extending slots defined therein around its circumference.

19. The contact configuration of claim 18 wherein the circumferentially oriented width of each slot is at least 10% to 40% of the circumference of the opening.

20. The contact configuration of claim 18 wherein at least some of the interstices between adjacent fibers are filled with a flexible, electrically insulating material.

21. The contact configuration of claim 18 wherein the socket is defined within an electronic apparatus configured to be implantable within a living body.

22. The contact configuration of claim 18 wherein the plug is defined upon an electrode line configured to be at least partially implantable within a living body.

23. A contact configuration for producing an electrical connection between a plug and a socket for an implantable medical device, the contact configuration including:
   a. a plug having an outer plug diameter,
   b. a socket having an inner socket diameter, the socket being configured to receive the plug,
   c. an electrically conductive contact section provided on the outer plug diameter, wherein the contact section:
      (1) includes fibers:
         i. having lengths oriented to define a planar fiber mat, with the plane of the mat being oriented substantially perpendicular to an insertion axis along which the plug travels when received within the socket, and
         ii. having free ends which extend radially outwardly from the plug to define an essentially circular outer contact section circumference; and
      (2) has an outer contact section diameter which is greater than an inner diameter of the portion of the socket wherein the plug is situated when the plug is fully inserted within the socket.

24. The contact configuration of claim 23 wherein the contact section is also provided on the inner socket diameter, and wherein the contact section on the inner socket diameter is formed of a layer of fibers:
   a. extending circumferentially about, and
   b. having free ends protruding radially inwardly from, the inner socket diameter.

25. The contact configuration of claim 23 wherein at least some of the interstices between adjacent fibers are filled with a flexible, electrically insulating material.

26. The contact configuration of claim 23 wherein:
   a. the socket is defined within an electronic apparatus configured to be implantable within a living body, and
   b. the plug is defined upon an electrode line configured to be at least partially implantable within the living body.

* * * * *